US00PP10657P

United States Patent [19]

Lemon

[11] Patent Number: Plant 10,657

[45] Date of Patent: Oct. 20, 1998

[54] VARIETY OF GERANIUM PLANT NAMED 'MORNING MIST'

[75] Inventor: David Lemon, Lompoc, Calif.

[73] Assignee: John Bodger & Sons Company, So. El Monte, Calif.

[21] Appl. No.: 821,260

[22] Filed: Mar. 20, 1997

Related U.S. Application Data

[63] Continuation of Ser. No. 571,107, Dec. 12, 1995, abandoned.

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 5,374 12/1984 Schumann ..... Plt./87.12

*Primary Examiner*—Howard J. Locker

*Attorney, Agent, or Firm*—Fulwider Patton Lee & Utecht, LLP

[57] ABSTRACT

The cultivar is characterized by its light salmon color. Its strong growth habit and free flowering provides for superb cuttings and also for quick recovery following wet weather conditions. The blooms are heat tolerant.

1 Drawing Sheet

BACKGROUND OF THE NEW PLANT

The present invention comprises a new and distinct cultivar of *Pelargonium×hortorum* known by the varietal name Morning Mist (Oglevee No. 72, Bodger No. 10GM 153-1). The new variety was discovered in a selective breeding program by David Lemon at Bodger Seeds, Ltd., Lompoc, Calif. The new variety is a selection from the crossing of Sunbelt Coral (U.S. Plant Pat. No. 5,757) which exhibits a different flower color from the claimed cultivar and which has a slower finishing time than the claimed cultivar, with Schone Helena (U.S. Plant Pat. No. 5,374).

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° fahrenheit night temperature, 72° fahrenheit day temperature, 72° fahrenheit vent temperature and grown in a soilless media of constant fertilizer 200 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Feb. 15, 1995 and flowered Apr. 1, 1995 under full light and greenhouse, and colorings were taken indoors under 200–220 foot candles of fluorescent cool white light using The R.H.S. Colour Chart of The Royal Horticultural Society of London.

The Plant

Classification:

*Botanical.*—*Pelargonium×hortorum.*

Form: Semi-dwarf mound.

*Height.*—14.0–15.0 cm from the media surface.

*Growth.*—Semi-dwarf; free branching; free flowering with semi-double flowers.

*Strength.*—Free standing.

Foliage: Stalked leaf attachment.

Leaves:

*Size.*—8.0–10.5 cm across; fully expanded leaf.

*Shape.*—Reniform; cordate base.

*Margin.*—Crenate.

*Texture.*—Slightly pubescent; slightly reflective.

*Color.*—Top: Green Group 137C; from the center to the edge of the leaf is Green Group 137A; Bottom: Green Group 137B.

*Ribs and veins.*—Palmate venation: Color: Yellow/Green group 147C.

Petioles:

*Length.*—5.5–6.5 cm.

*Color.*—Yellow/green group 147C.

Stem:

*Color.*—Yellow/green group 147C.

*Internodes.*—1.5–2.5 cm in length.

The Bud

Shape: Upright; hemispherical cluster.

Size: 2.5–4.0 cm across.

Inflorescence

Blooming habit: Free and early flowering; semi-double; slow to shatter.

Size: 10.0–13.0 cm across.

Borne: Umbel; florets on pedicel; pedicle on peduncle; 4.0–8.0 cm above foliage.

Florets: 31–36 florets per inflorescence. Closed: Bud size: 1.0–1.2 cm; elliptical; bud showing faintest tint of color.

Open:

*Form.*—Flat to slightly cupped.

*Color.*—Top: Upper three petals Red Group 39B; Bottom petals: Red Group 38A; Bottom Red Group 39C.

*Petals.*—5–9 in number; separate, not united; margin entire; obovate; flat to slightly cupped.
*Size.*—3.6–4.3 cm across.
*Texture and appearance.*—Smooth, slight reflective. Appearance from a distance is a light salmon flower above medium green foliage.

Petaloids:
*Quantity.*—0–2.
*Shape.*—Narrow, flat, twisted. Some form fans of 2–3 lobes.
*Color.*—Top: Red Group 39C; Bottom: Red Group 38C.

Pedicel:
*Length.*—2.0–3.5 cm.
*Color.*—Yellow-Green Group 147C.

Peduncle: Arise from node opposite the leaf petiole.
*Length.*—12.5–16.0 cm.
*Color.*—Yellow-Green Group 147C.

Persistence:
*Disease resistance.*—Not known.
*Lasting quality.*—Not known.

Reproductive Organs

Stamens:
*Anthers.*—2.0–4.0 mm in length.
*Filaments.*—5.0–8.0 mm in length.
*Pollen.*—Golden Brown.

Pistils:
*Number.*—One.
*Length.*—8.0–9.0 mm.
*Stigma.*—5–6 parted, red purple color.
*Style.*—3.0–5.0 mm, red purple color.

Ovaries: Superior; pubescent; pale green in color; 2.0–2.5 mm in length.

Fruit: None.

General Characteristics

Morning Mist is a new light salmon variety similar in color to the commercial variety Pink Camellia. Furthermore, unlike Pink Camellia (unpatented) which has a different flower color and which has a lower cutting yield and slowing rooting speed than Morning Mist, this variety exhibits a strong growth habit, branches freely and roots easily. It is heat tolerant in the outdoor garden, free flowering and recovers quickly following wet weather conditions. Given all these positive properties, this variety should please both the grower and the gardener.

I claim:

1. A new and distinct variety of geranium plant, substantially as shown and described.

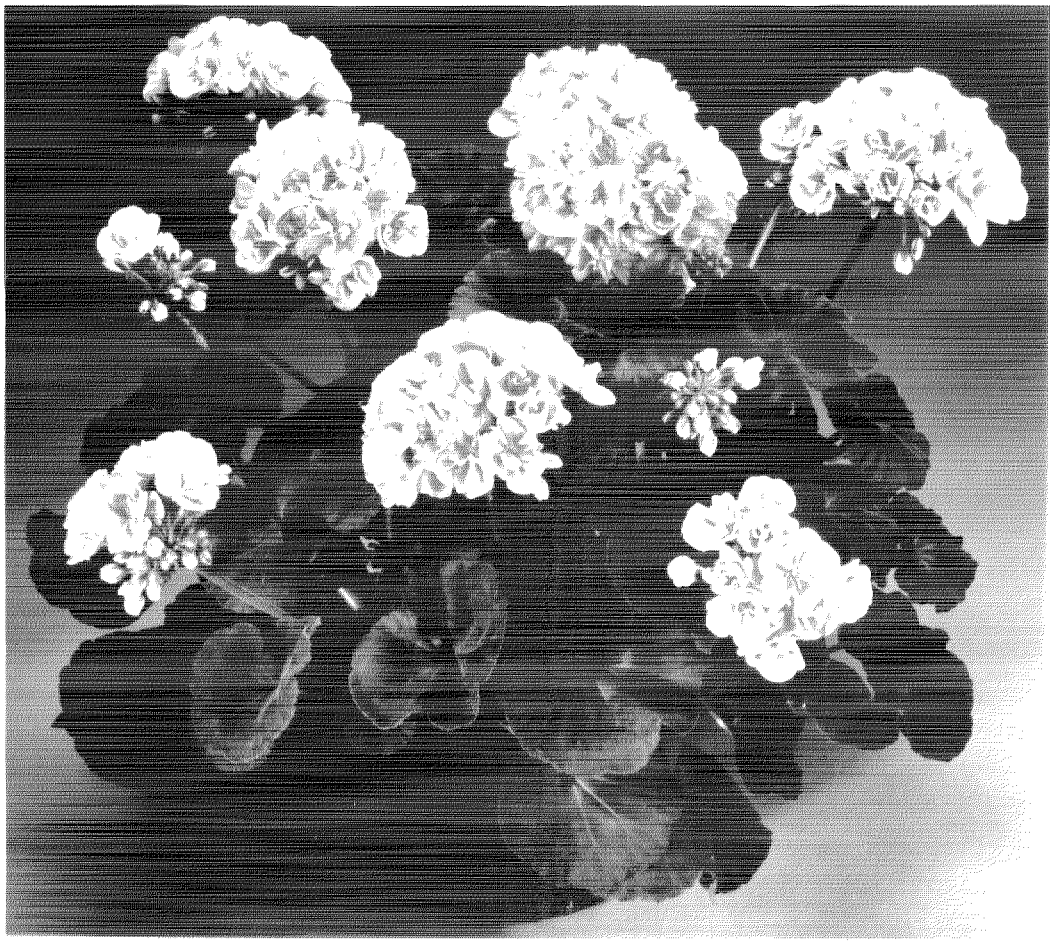

* * * * *